(12) United States Patent
Joshi et al.

(10) Patent No.: US 6,174,837 B1
(45) Date of Patent: Jan. 16, 2001

(54) METHOD FOR TREATING PLANTS

(75) Inventors: Jagmohan Joshi; Mark A. Holland, both of Salisbury, MD (US)

(73) Assignees: Salisbury State University, Salisbury; University of Maryland Eastern Shore, Princess Ann, both of MD (US)

( * ) Notice: Under 35 U.S.C. 154(b), the term of this patent shall be extended for 0 days.

(21) Appl. No.: 09/342,058

(22) Filed: Jun. 29, 1999

Related U.S. Application Data

(60) Division of application No. 09/031,599, filed on Feb. 27, 1998, now Pat. No. 5,961,687, which is a continuation-in-part of application No. 08/686,659, filed on Jul. 26, 1996, now abandoned.

(51) Int. Cl.[7] .................................................. A01N 63/00
(52) U.S. Cl. .......................................................... 504/117
(58) Field of Search ............................................. 504/117

(56) References Cited

U.S. PATENT DOCUMENTS

| | | | |
|---|---|---|---|
| 4,581,056 | 4/1986 | Nooden et al. | 71/28 |
| 5,268,171 | 12/1993 | Polacco et al. | 424/93 D |
| 5,512,069 | 4/1996 | Holland et al. | 47/57.6 |
| 5,532,204 | 7/1996 | Joshi | 504/118 |

OTHER PUBLICATIONS

Hemming, et al. "Effect of Methanol on Plant Respiration", J. Plant Physiol. vol. 146, pp. 193–198 (1995).

Fall, et al., "Leaf Methanol—the Simplest Natural Product from Plants", Trends in Plant Science, vol. 1, No. 9, PP. 296–300, Sep. 1996.

Basile, et al., "Vitamin $B_{12}$–Stimulated Growth and Development of *Jungermannia leiantha* Grolle and *Gymnocolea inflata* (Huds.) Dum. (Hepaticae)", The Biologist, vol. 88(2), pp.77–81 (1985).

Devlin, et al., "Influence of Methanol on Plant Growth", PGRSA Quarterly, vol. 22, No. 4, pp. 102–107, (1994).

Mitchell, et al. "Plant Performance and Water Use of Peppermint Treated with Methanol and Glycine", Journal of Plant Nutrition, 17(11), 1955–1962 (1994).

Li, et al., "Effect of Methanol on Soybean Photosynthesis and Chlorophyll", Journal of Plant Nutrition, 18(9), 1875–1880 (1995).

Devlin, et al., "The Effect of Methanol on the Growth and Pigment Content of Bachelor's–Button (*Centaurea cyanus*) and Ge–anium"PGRSA Quarterly, vol. 23, No. 2, pp. 127–135 (1995).

Freyermuth, et al., "Metabolic Aspects of Plant Interaction with Commensal Methylotrophs", M.E. Lidstrom and F. R. Tabita (eds.), Microbial Growth on $C_1$ Compounds, 277–284 (1996).

Nishio, et al., "Physiological Aspects Of Methanol Feeding to Higher Plants", 1993 Proceedings of Twentieth Annual Meeting, Plant Growth Regulator Society of America, pp. 8–13.

Holland, et al., "Urease–Null and Hydrogenase–Null Phenotypes of a Phylloplane Bacterium Reveal Altered Nickel Metabolism in Two Soybean Mutants", Plant Physiol. (1992) 942–948.

(List continued on next page.)

*Primary Examiner*—S. Mark Clardy
(74) *Attorney, Agent, or Firm*—Arent Fox Kintner Plotkin Kahn

(57) ABSTRACT

The present invention provides a method for increasing productivity of a plant by spraying Pink Pigmented Facultative Methylotroph (PPFM) on a plant. The invention also relates to increasing productivity of a plant under stress by applying Pink Pigmented Facultative Methylotroph (PPFM) to a plant and subsequently applying an aqueous solution containing methanol to the plant.

11 Claims, 1 Drawing Sheet

OTHER PUBLICATIONS

Holland, "PPFMs and Other Covert Contaminants: Is There More to Plant Physiology Than Just Plant?", Annu. Rev. Plant Physiol. Plant Mol. Biol. (1994), 45:197–209.

Stebbins et al., "Genetic Tests of the Roles of the Embryonic Ureases of Soybean", Plant Physiol., vol. 97, pp. 1004–1010 (1991).

Corpe, W.A. et al., "Methanol–Utilizing Bacteria Associated with Green Plants", Proceedings of the Thirty–Eight General Meeting of the Society for Industrial Microbiology, vol. 23, p 483–493 (1982).

H.D. Sunderman et al., "Soybean Response to Foliar Applied Methanol in Humid and Semiarid Environments", J. Prod. Agric., vol. 10, No. 3, pp. 415–418 (1997).

S.L. Albrecht et al. "Effects of Foliar Methanol Applications on Crop Yield", Crop Science, vol. 35, No. 6, pp. 1642–1646 (1995).

METHOD FOR TREATING PLANTS

CROSS-REFERENCE TO RELATED APPLICATIONS

This application is a Divisional of Application Ser. No. 09/031,599, now U.S. Pat. No. 5,961,687, filed February 27,1998, which is a continuation-in-part of U.S. Application Ser. No. 08/686,659, filed Jul. 26, 1996.

BACKGROUND OF THE INVENTION

1. Field of the Invention

The present invention provides a method for treating plants by spraying plants with Pink Pigmented Facultative Methylotroph (PPFM) either alone or in combination with methanol during growth.

2. Discussion of the Background

Improvements in crop yields is a highly active area of research, and as a result, today's farms are much more productive than their counterparts from a century ago. However, as the world's population increases with a concomitant decrease in farming resources, more and more emphasis is being placed on enhancing crop yields. Farmers are presently seeking ways to expand their yields while limiting the use of dangerous fertilizers and pesticides. An avenue of research which has developed from the desire to avoid harmful chemical crop treatments is the treatment of seeds or the soil with non-toxic crop augmenter prior to sowing.

Schroth et al, U.S. Pat. No. 4,849,008, describes enhancing root crop yields by treating plant seeds with a specific growth promoting bacterial strain of the genus Pseudomonas. The bacterial strains may be applied with a liquid carrier or in a paste.

Williams, U.S. Pat. No. 5,106,648, refers to a method of preparing coated seeds by slurrying seeds with a microorganism, which has a beneficial effect on plants which grow from these seeds, a carrier medium and an adhesive polymer. This method is supposed to maintain microorganisms viable for extended periods of time.

Mann, U.S. Pat. No. 4,061,488, addresses treatment of plant seeds with spores from *Bacillus uniflagellatus* to enhance plant growth. It is suspected that root growth triggers the germination of these spores.

Polacco et al, U.S. Pat. No. 5,268,171, describe a method of altering the metabolism of a plant includes the steps of genetically altering at least one commensal bacterium of the plant to alter the level and nature of urease activity produced by the plant.

Holland et al, U.S. Pat. No. 5,512,069, which is incorporated herein in its entirety, describes methods for increasing the germination of seeds by coating or impregnating them with PPFMs. PPFMs were first described in connection with plants more than 20 years ago when it was demonstrated that cell cultures of the leafy liverwort Scapania are routinely associated with PPFMs (Basile et al, 1985, The Bryologist 88(2):77). Since then these bacteria have been shown to be universally associated with plants, but the exact nature of the relationships has remained obscure.

Nonomura and Benson, Proc. Nat'l. Acad. Sci. U.S.A., 89, 9794 (1992) teach that foliar sprays of aqueous (10–50%) methanol increased growth and yield of C3 crop plants in arid environments.

Nishio et al, in Proceedings of Twentieth Annual Meeting Plant Growth Regulator Society of America, Ferguson, ed., pp. 8–13, 1993, teach that a 30% increase in dry matter and accelerated rate of development of soybean plants can be achieved with a foliar-applied 15% methanol with fertilizer on a daily rotated basis.

Moore et al, U.S. Pat. No. 4,297,130 teach a method for the foliar feeding of leguminous plants with a nonburning nitrogenous plant food which is applied to the foliage of he plant at the R1–R4 flowering stage.

Joshi, U.S. Pat. No. 5,532,204, which is incorporated by reference herein in its entirety, teaches a method of fertilizing leguminous plants for increase yield using methanol and urea based nitrogen fertilizer.

Despite these teachings, the use of methanol has not become routine in commercial application. Two reasons for this may be that (1) the treatment is not universally effective under all cultural conditions or on all crops; and (2) the mechanism by which methanol works to affect yield has not been demonstrated convincingly.

Because methanol applications seemed to be most effective under high light conditions and in C3 plants, it was suggested that methanol works by inhibiting photorespiration (Nonomura et al, 1992, Proc. Natl. Acad. Sci. USA 89:9794–9798). This idea was supported by the observations that the treatment was enhanced by the addition of glycine to the spray mixture and that C4 plants (in which photorespiration is already low) did not respond. Fall and Benson (1996, Trends in Plant Sci. 1: 296–301) have elaborated on this explanation, suggesting possible alterations in metabolism that would result in a greater than normal return of photorespiratory carbon to the chloroplast. However, further studies have complicated the picture, and thus the mechanism by which methanol affects plant growth is not clear.

Moreover, despite the above knowledge, producers of crop plants report "hit or miss" success with the above methods. Accordingly, a method which provides reproducible increases in growth and yield is desirable.

SUMMARY OF THE INVENTION

Accordingly, one object of this invention is to provide a novel method for treating plants which will result in increased yield and/or growth.

One object of the invention is to provide a method for increasing plant productivity (growth and yield) by applying a PPFM to a plant.

Another object of the invention is to provide a method for increasing plant productivity (growth and yield) by applying a PPFM to a plant, followed by applying an aqueous solution of methanol and nitrogen to the plant.

Yet another object of the invention is to provide a method for increasing the productivity (growth and yield) of a plant under stress by applying a ppfm to a plant, followed by applying an aqueous solution of methanol and nitrogen to the plant.

With the foregoing and other objects, advantages and features of the invention that will become hereinafter apparent, the nature of the invention may be more clearly understood by reference to the following detailed description of the preferred embodiments of the invention and to the appended claims.

DESCRIPTION OF THE PREFERRED EMBODIMENTS

Figure 1:
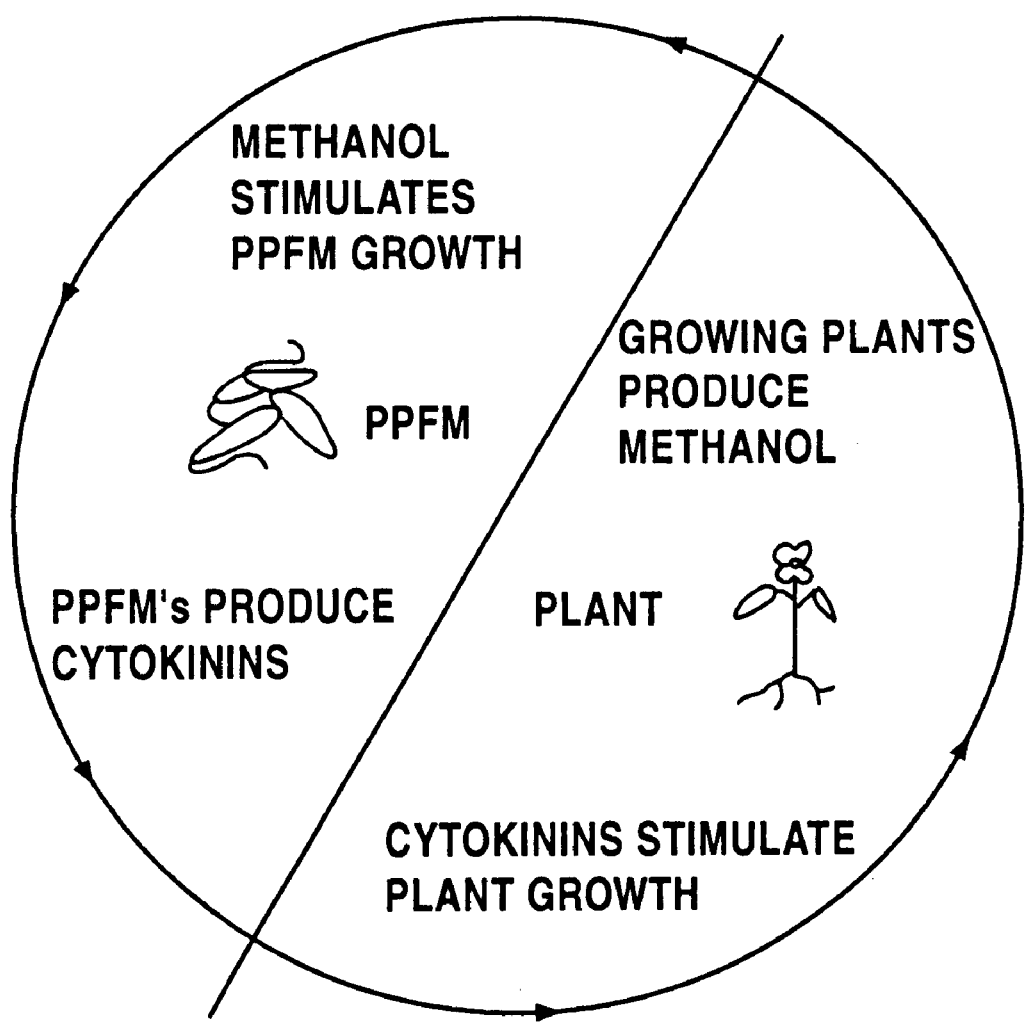
FIG. 1 shows a possible model for how PPFM bacteria mediate the effect of methanol on plants.

PPFMs have been reported from virtually all land plants examined. Corpe, J. Microbiol. Methods, 3:215–221 (1985).

Members of all plant phyla contain associated PPFMS. While other non-pink methylotrophs are also associated with plants, PPFMs are the most persistent and are the predominant phylloplane methylotrophs. PPFMs have the following characteristics: (1) they are facultative methylotrophs; (2) they are distributed ubiquitously on plants; (3) they are present in large numbers; (4) they stimulate plant growth in vitro; (5) they participate in plant nitrogen metabolism; (6) they enhance seed germination; (7) they stimulate root growth; and (8) they manufacture cytokinins.

Suitable plants include any plant such as field crops, flowering plants (leguminous plants especially), conifers (pine trees), etc. Preferred leguminous plants include peanut, bean, pea and soybean.

The inventors have found PPFMs in all soybean tissues, including seed and callus. The inventors classify PPFMs as Methylobacterium spp., not only by their methylotrophy and pink pigmentation, but also due to restriction analysis of PCR-amplified 16S rRNA genes. Tsuji et al, J. Gen. Microbiol. 136:1–10 (1990). PPFMs isolated from soybean most closely resemble *M. mesophilicum* while isolates from other plants group include such members as *M. organophilum* and *M. extorquens*. Thus, the term PPFM as used herein is intended to encompass all pink pigmented facultative methylotroph bacteria. It should be understood that both naturally occurring, mutagenized and recombinantly obtained bacterial can be used.

In a preferred embodiment, the PPFM is at least one PPFM selected from the group consisting of *M. mesophilicum, M. organophilum* and *M. extorquens*. In a more preferred embodiment, *M. mesophilicum* is used.

PPFMs can be applied onto plant foliage, onto plant seeds or onto the soil in which plants will be propagated.

In a first embodiment, PPFMs are applied to a plant at least once during the R1–R8of growth. Critical stages of growth of plants (soybeans) are described by Fehr et al, "Stages of Soybean Development", Iowa Sate University Press: Ames, Iowa, 1977. Preferably, viable PPFMs should be present in an amount effective to increase the productivity (either yield or growth) of the plant by at least 1% compared with an untreated plants. More preferably, viable PPFMs should be present in an amount effective to increase the productivity of the plant by at least 2% compared with an untreated plant. Most preferably, viable PPFMs should be present in an amount effective to increase the productivity of the plant by at least 5% compared with an untreated plant. Preferably, bacterial concentration of $10^5$ to $10^{10}$ bacterial cells/ml is considered a desirable range, although optimum values for specific plants and bacteria may be empirically determined.

In a second embodiment, PPFMs can be applied to plant seeds. The application of PPFMs to the seeds of plants can consist of coating seeds using known coating procedures such as those described in U.S. Pat. No. 5,106,648, the contents of which are incorporated herein by reference. For example, seeds may be coated by slurrying seeds with the a solution of PPFMs and air drying the resulting product, preferably at a temperature not greater than 30° C.

The proportion of composition to seed may be selected from the range of 0.1 to 25% by weight of the seed, preferably, 0.5 to 5% by weight and most preferably 0.5 to 2.5% by weight, depending on the type of seed.

Alternatively, seeds can be immersed in a solution of PPFM such that a portion of the solution enters the seeds. Thereafter, the seeds can be planted or dried for later planting. Alternatively, PPFMs can be delivered to the seeds by vacuum infiltration or under pressure.

Viable PPFMs should be present in the coated seeds in an amount effective to increase the germinability of a seed lot (e.g., 50 seeds) by at least 0.5% compared with an uncoated seed lot. Preferably, viable PPFMs should be present in an amount effective to increase the germinability of a seed lot by at least 1% compared with an uncoated seed lot. More preferably, viable PPFMs should be present in an amount effective to increase the germinability of a seed lot by at least 2% compared with an uncoated seed lot. Most preferably, viable PPFMs should be present in an amount effective to increase the germinability of a seed lot by at least 5% compared with an uncoated seed lot. In preferred coatings, bacterial concentration of $10^5$ to $10^{10}$ bacterial cells/ml is considered a desirable range, although optimum values for specific seeds and bacteria may be empirically determined.

Treated seeds are then planted and grown under normal conditions. Alternatively, PPFMs can be applied to plants at any stage of their development. Conventional spraying techniques can be used. The PPFMs can be administered prior to, after, or concurrently with the methanol application.

In a third embodiment, PPFMs are applied to the soil in which the seed will be sown. Seeds are then sown in the treated soil.

The application of methanol and nitrogen is conducted at least once during the R1–R8, preferably R3–R5 stage of growth. Critical stages of growth of soy bean, a leguminous plant, are described by Fehr et al, "Stages of Soybean Development", Iowa Sate University Press: Ames, Iowa, 1977.

A suitable aqueous solution of methanol and nitrogen in accordance with the present invention is described in U.S. Pat. No. 5,532,204.

The amount of methanol ($M_1$) in the aqueous solution is from 10–50 v/v % based on the total volume of water. The amount of methanol applied to the foliage is 50 to 150, preferably 62.5 to 125, L ha$^{-1}$. Other alcohols can be substituted for methanol such as ethanol, propanol, and butanol.

The amount of nitrogen ($N_1$) in the aqueous solution is from 10–100, preferably 10–25, most preferred 12.5, Kg ha$^{-1}$ Suitable nitrogen sources include urea such as contained in urea based fertilizers. Other nitrogen sources can be used.

The ratio of $M_1$:$N_1$ is preferably 2.5:1.

The solution may contain further nutrients such as potassium and phosphorous. Particularly suitable sources of these nutrients are such as potassium phosphate and potassium polyphosphate. Phosphorous and potassium are each ordinarily used in amounts less than about 5 w/v %, based on the volume of the solution.

The solution containing methanol and nitrogen is suitably sprayed on the plant using conventional means.

Having now fully described the invention, it will be apparent to one of ordinary skill in the art that many changes and modifications can be made thereto without departing from the spirit or scope of the invention as set forth herein.

EXAMPLES

Example 1

Application of PPFMs to plants was performed in accordance with the methods detailed in U.S. Pat. No. 5,512,069. Application of methanol to seeds was performed in accordance with U.S. Pat. No. 5,532,204.

Soybeans were treated with dry heat before planting to lower the population of PPFMs on them (see U.S. Pat. No. 5,512,069). Untreated seeds served as controls.

Under non-stressed (freely watered) conditions, application of methanol does not affect plant dry weight (a measure of yield), regardless of whether PPFMs are present.

| Treatment | Mean dry weight +/− SD (g) | % gain over controls |
|---|---|---|
| PPFMs present, Methanol applied | 6.85 +/− 1.69 | 78 |
| PPFMs absent, Methanol applied | 5.03 +/− 1.19 | 80 |

Under stress (wilting) conditions, application of methanol improves growth (increase in plant dry weight) only when PPFMs are present.

| Treatment | Mean dry weight +/− SD (g) | % gain over controls |
|---|---|---|
| PPFMs present, Methanol applied | 4.64 +/− 0.72 | 65 |
| PPFMs absent, Methanol applied | 2.69 +/− 0.65 | 6 |

The data show that when plants are not under water stress, the presence or absence of PPFM bacteria is not an important factor in determining growth rate following the application of methanol. Cured and uncured plants gained 80% and 78% in dry weight during the course of the experiment. When plants are water stressed, however, methanol is effective in stimulating growth only when PPFMs are present. Cured plants under stress gained only 6% in dry weight while plants with PPFMs gained 65% dry weight. Thus, PPFMs and methanol exhibit a synergistic effect on plants under stressed conditions.

Example 2

To test the effects of foliar applications of methanol on soybean (*Glycine max* (L.) Merr. cv. 'Corsica'(maturity group IV)), field experiments were conducted over three years. In the first year, methanol at 0, 62.5 and 125 liters× $ha^{-1}$ was combined with urea nitrogen at 0, 12.5 and 25 kg× $ha^{-1}$ and sprayed with distilled water in a total volume of 500 liters× $ha^{-1}$ on test plants at the R5 stage of development. Latron B-1956 (Rohm and Haas) surfactant at 0.1% was included in all treatments. Treatments were applied from a knapsack sprayer in a randomized complete block design with four replications. Test blocks measured 5 m×1.52 m (7.6m²). Plants were harvested by hand, threshed, and seed yield determined by weight. All seed weights are reported at 13% moisture content. In subsequent years, only the concentration of methanol (62.5 liters× $ha^{-1}$) and urea (12.5 kg× $ha^{-1}$) found to be most effective in the first year were used as methanol and nitrogen treatments in field experiments.

To test the effects of foliar applications of methanol and/or nitrogen on PPFM populations, the numbers of these bacteria on leaves from plants in field experiments of the second and third years were assayed. For the assay, leaves from four plants in each of the four replications of each treatment were harvested one week after spraying. Leaf material was rinsed, then ground in distilled water in a mortar and pestle. Serial dilutions of the grindate were plated on ammonium mineral salts (AMS) medium (Cote, R., ed. 1984, ATCC Media Handbook (American Type Culture Collection, Rockville, Md.) solidified with 15 g per liter Bacto-agar (Difco) and containing 15 µg per ml cycloheximide to reduce contamination from fungi. Plates were incubated at room temperature for 10 days before counting. Colony counts of PPFM bacteria were used to calculate colony-forming units per gram fresh weight of plant tissue (cfu/gfw).

To test whether PPFMs applied to leaves can substitute for methanol, spray applications of the bacterial alone and in combination with methanol were included in field experiments in the third year. Experiments were conducted as described above with the following treatments tested: distilled water (control), methanol plus urea, methanol plus PPFM bacteria ($1\times10^{15}$ cfu× $ha^{-1}$), and PPFM bacteria ($1\times10^{15}$ cfu× $ha^{-1}$) alone. The bacteria used in these treatments were isolated from soybean seed coat on plates of AMS medium. From a single bacterial colony, a liquid culture in the same medium was established and used to inoculate 12 liter batches of the bacteria in a Microferm fermentor (New Brunswick Scientific). Cells were harvested by centrifugation and resuspended in distilled water for application to plants in the field.

To test whether the presence of PPFM bacteria is required for foliar applications of methanol to be effective, greenhouse experiments were conducted. Seeds of soybean were cured of their PPFM bacteria with dry heat as previously described (Holland et al, 1992, Plant Physiol 98:942–948)). Cured and untreated seeds were then plated in the greenhouse in a soil-less potting medium (Pro-Mix BX), Premier Horticulture Inc.). During germination, and while the seedlings established themselves, all plants were watered freely. After 4 weeks, both cured and untreated plants were divided into two groups (each group consisting of approximately 10 pots of 5 plants). One group of cured-seedlings and one group of untreated seedlings were maintained as before under freely-watered conditions. The remaining plants were watered sparingly—and only when the plants showed signs of wilting. After 2 weeks, half of the plants in each test group were harvested and dried to constant weight (a zero-time control). The remaining plants were sprayed with methanol (0.5 ml per plant) from an atomizer and were allowed to continue growing under their respective watering regimes for an additional 2 weeks. At the end of this period, all remaining plants were harvested and dried to constant weight.

As shown in Table 1 below, data from the first year show that methanol produced statistically significant increased in yield when applied at a rate of 62.5 liters× $ha^{-1}$, except in combination with high nitrogen (urea nitrogen at 25 kg× $ha^{-1}$). Methanol at a rate of 125 liters× $ha^{-1}$ was effective in combination with urea at 12.5 kg× $ha^{-1}$. Highest yields were obtained from plants treated with methanol (62.5 liters× $ha^{-1}$) and urea (12.5 kg× $ha^{-1}$). This combination was used in all subsequent field experiments.

TABLE 1

| Treatment | $M_0$ | $M_1$ | $M_2$ |
|---|---|---|---|
| $N_0$ | 2.00 | 2.59* | 2.28 |
| $N_1$ | 2.18 | 2.94* | 2.57* |
| $N_2$ | 2.15 | 2.36 | 2.32 |

*statistically different from $M_0N_0$ control ($p<0.05$)
$LSD_{0.05}$ = 0.37
$M_0$ = 0 methanol, $M_1$ = 62.5 liters × $ha^{-1}$ methanol, $M_2$ = 125 liters × $ha^{-1}$ methanol $N_0$ = 0 urea; $N_1$ = 12.5 kg × $ha^{-1}$ urea, $N_2$ = 25 kg × $ha^{-1}$ urea (Experiment conducted in first year)

To assess the effect of methanol and urea on PPFM populations, counts of the bacteria were made from leaves following treatment. As illustrated in Table 2 below, treatments of urea, methanol, and the combination all resulted in statistically significant increases in the numbers of PPFMs on leaves. Leaf PPFM populations were also examined by a leaf print method (Corpe, 1985, J. Microbiol. Methods, 3:215–221) that allowed assessment of the relative abundance of the bacteria on leaf tops vs. bottoms. These prints showed that the increase in PPFM numbers following spray treatment was primarily due to increases of the bacteria on the tops of leaves—the surfaces to which the treatment was applied. Yields from treated plants were also measured (Table 2) and showed the same pattern of increase achieved in the first year experiments. More significantly, the increases in yield correlate with the increases in PPFM numbers ($R^2 = 0.88$).

TABLE 2

| Treatment | $M_0$ | $M_1$ |
|---|---|---|
| $N_0$ | 2.00 | 2.4* |
|  | [$0.1 \times 10^5$] | [$1.5 \times 10^5$] |
| $N_1$ | 2.4 | ? |
|  | [$1.6 \times 10^5$] | [$1.8 \times 10^5$] |

*statistically different from $M_0N_0$ control ($p<0.05$)
$LSD_{0.05)}$ = for yield data
$LSD_{0.05)}$ = $0.3 \times 10^5$ for PPFM data
$M_0$ = 0 methanol, $M_1$ = 62.5 liters × ha$^{-1}$ methanol, $N_0$ = 0 urea, $N_1$ = 12.5 kg × ha$^{-1}$ urea (Experiment conducted in second year)

Field experiments in the third year tested whether PPFM bacteria applied directly to the leaves of soybean could substitute for applications of methanol. Table 3 summarizes the data from these experiments. When PPFMs were applied either alone or in combination with methanol, yield increases of 70% over controls resulted. Treatments that included the bacteria were more effective than treatment with methanol and urea.

TABLE 3

| | Treatment | | | | |
|---|---|---|---|---|---|
| | $M_0N_0$ | $M_1N_1$ 2.00 | $M_1$, PPFMs | PPFMs | |
| Yield | 1.35 | 1.73 | 2.35 | 2.34 | Mean = 1.94 |
|  |  |  |  |  | $LSD_{0.05)}$ = 0.17 |
| cfu/gfw PPFMs | 0.7 × 10$^5$ | 1.3 × 10$^5$ | 1 × 10$^5$ | 1.7 × 10$^5$ | Mean = $1.2 \times 10^5$ $LSD_{0.05)}$ = $0.2 \times 10^5$ |

$M_0$ = 0 methanol, $M_1$ = 62.5 liters × ha$^{-1}$ methanol, $N_0$ = 0 urea, $N_1$ = 12.5 kg × ha$^{-1}$ urea, PPFMs = $1 \times 10^{15}$ cfu × ha$^{-1}$ PPFMs (Experiment conducted in third year)

Although not intending to be bound by theory, the above described data suggests that methanol works by stimulating the growth of PPFMs resident on the plant. Not only does the increase in their numbers that follows application of methanol correlate with yield increases, but in the absence of the bacteria methanol does not stimulate growth. Furthermore, increasing the numbers of PPFMs on leaf surfaces by applying them directly produces the same effect on yield as applying methanol.

These results support a model that explains how PPFM bacteria mediate the effect of methanol on plants as follows (see FIG. 1):

(1) Foliar application of methanol stimulates the growth of PPFM bacteria resident on plant leaves. Under high light and low water potential, neither plant nor bacteria are growing. Applied methanol is perceived by the bacteria as a sign that the plant is growing. In response to this signal, the bacteria themselves begin to grow.

(2) Growing PPFM bacteria produce cytokinins (Freyermuth et al, 1996, in Microbial Growth on C1Compounds, eds. Lidstrom, ME and Tabita,FR (Kluwer, Dordrecht), pp. 277–284).

(3) The cytokinin signal is perceived by the plant as signal for growth (Holland, 1997, Plant Physiol, 115:865–5868).

(4) The plant grows, producing additional methanol as a waste product (Obendorf, 1990, J. Exp. Bot. 41:489–495).

(5) PPFM bacteria are stimulated to continue to grow by the methanol produced by the plant.

(6) The cycle continues.

This proposed mechanism suggests that applied methanol is responsible for initiating a cycle of cross-talk between bacteria and plant that results in enhanced growth and yield even under poor growing conditions.

What is claimed as new and is desired to be secured by Letters Patent of the United States is:

1. A method of increasing productivity of plants under stress which comprises the steps of:

applying to a seed or foliage of a plant Pink Pigmented Facultative Methylotroph (PPFMs), and applying an aqueous solution comprising an alcohol and a nitrogen source to foliage of said plant.

2. The method of claim 1, wherein said alcohol is methanol.

3. The method of claim 1, wherein said plant is a bean, pea, soybean or peanut plant.

4. The method of claim 1, wherein said PPFM is selected from the group consisting of *M. mesophilicum, M. organophilum, M. extorquens* and mixtures thereof.

5. The method of claim 4, wherein said PPFM is *M. mesophilicum*.

6. The method of claim 2, wherein said aqueous solution comprises 1–50 v/v % methanol.

7. The method of claim 1, wherein said nitrogen source is urea.

8. The method of claim 2, wherein the ratio of methanol to nitrogen is 2.5:1.

9. The method of claim 2, wherein the amount of methanol applied to said plant is from 50 to 150 L ha$^{-1}$.

10. The method of claim 1, wherein the amount of nitrogen applied to said plant is from 10–100 Kg ha$^{-1}$.

11. The method of claim 1, wherein said PPFMs are applied to seeds of said plant and thereafter said aqueous alcoholic solution is applied to plants propagated from said seeds.

* * * * *